United States Patent
Hoffman

(10) Patent No.: US 9,373,065 B1
(45) Date of Patent: Jun. 21, 2016

(54) PAPER FEED SYSTEM AND METHOD

(71) Applicant: Express Scripts, Inc., St. Louis, MO (US)

(72) Inventor: Robert E. Hoffman, Linden, IN (US)

(73) Assignee: Express Scripts, Inc., St. Louis, MO (US)

( * ) Notice: Subject to any disclaimer, the term of this patent is extended or adjusted under 35 U.S.C. 154(b) by 0 days.

(21) Appl. No.: 14/793,840

(22) Filed: Jul. 8, 2015

(51) Int. Cl.
  *G06F 15/00* (2006.01)
  *G06K 15/00* (2006.01)
  *G06K 1/00* (2006.01)
  *G06K 15/16* (2006.01)
  *G06K 15/02* (2006.01)

(52) U.S. Cl.
  CPC .............. *G06K 15/16* (2013.01); *G06K 15/021* (2013.01)

(58) Field of Classification Search
  USPC .................................................. 358/1.1–1.18
  See application file for complete search history.

(56) References Cited

U.S. PATENT DOCUMENTS

| | | | |
|---|---|---|---|
| 3,747,917 A | 7/1973 | Roda | |
| 3,973,373 A | 8/1976 | Williams | |
| 6,817,605 B1 | 11/2004 | Bohn | |
| 7,152,856 B2 | 12/2006 | Kamiya et al. | |
| 7,326,166 B2 | 2/2008 | Sytema | |
| 7,489,898 B2 | 2/2009 | Hayashi | |
| 8,113,499 B2 | 2/2012 | Kushida et al. | |
| 2002/0025207 A1 | 2/2002 | Yoshie et al. | |
| 2005/0125097 A1* | 6/2005 | Chudy et al. | 700/236 |
| 2010/0314049 A1 | 12/2010 | Yamauchi et al. | |
| 2013/0098985 A1* | 4/2013 | Chambers | 235/375 |

* cited by examiner

*Primary Examiner* — Douglas Tran
(74) *Attorney, Agent, or Firm* — Husch Blackwell LLP

(57) ABSTRACT

A pharmaceutical filling system for a high volume pharmacy is described. The system can include a paper feed device and method. The system may include a paper collator with at one selectively openable shelf. A control device may monitor the capacity of the selectively openable shelf, and instruct a printer to hold printing additional print jobs. The selectively openable shelf may then be opened to allow the printed literature resting thereon to fall to a lower shelf, and the printer can then be restarted. Sheets of printed literature may be drawn from the paper collator, collected with any other sheets of printed literature associated with a prescription order, and mated with the prescription order for shipment.

20 Claims, 16 Drawing Sheets

PAPER FEED SYSTEM AND METHOD

FIELD

The present application relates generally to the technical field of automated filling centers. In a specific example, the present application may relate to a high volume fulfillment center, e.g., a high volume pharmacy and to systems and devices used in filling prescriptions and prescription orders at a high volume pharmacy.

BACKGROUND

A high-volume pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

DETAILED DESCRIPTION

Example systems and methods for literature and paper handling (e.g., in a pharmacy) are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a high volume pharmacy. The prescription order may include more than one prescription drug for fulfillment. Each prescription drug in a prescription order is an order component of the prescription order. Generally, the order components are pill bottles or other packaging having a quantity of a prescription drug contained therein.

The prescription drugs may be dispensed at various sections of the high volume pharmacy. Some prescription orders may require manual fulfillment of order components. Distribution of order components necessitating manual fulfillment is provided by a distribution section and one or more manual sections. In general, manual handling includes manual fulfillment of prescription drugs. Manual handling occurs at one or more than one manual sections, from which the order component exits the manual fulfillment device. Some prescription orders may be filled using automated machines, which can fill prescription orders at a greater rate than manual fulfillment.

Figure 1:
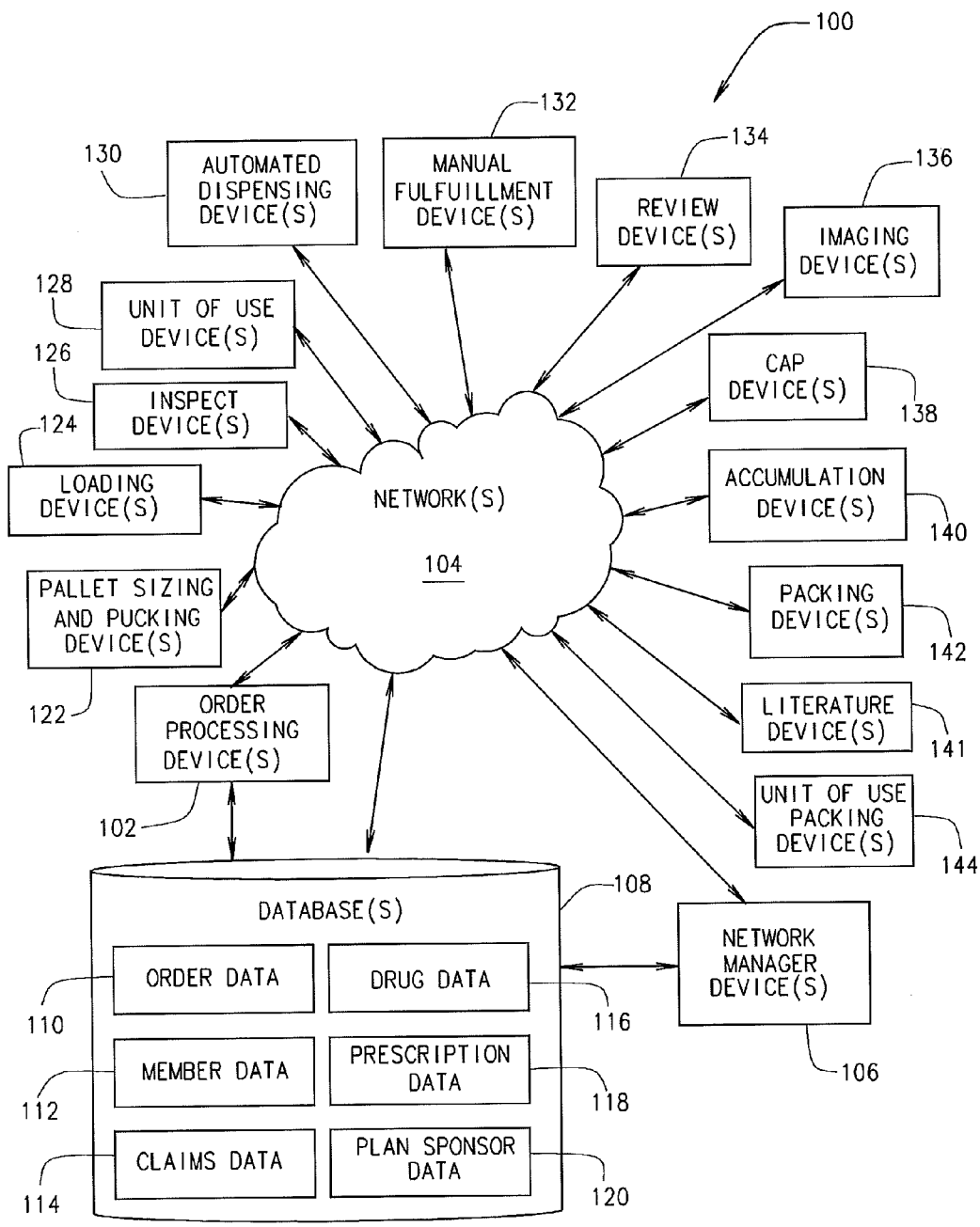
FIG. 1 is a block diagram of an example system, according to an example embodiment.

FIG. 1 is a block diagram of an example system 100, according to an example embodiment. While the system 100 is generally described as being deployed in a high volume pharmacy or fulfillment center (e.g., a mail order pharmacy, a direct delivery pharmacy, and the like), the system 100 and/or components thereof may otherwise be deployed. The system 100 may include an order processing device 102 in communication with a benefit manager device 106 over a network 104. Additional devices which may be in communication with the benefit manager device 106 and/or the order processing device 102 over network 104 include: database(s) 108 which may store one or more than one of order data 110, member data 112, claims data 114, drug data 116, prescription data 118, and plan sponsor data 120; pallet sizing and pucking device(s) 122; loading device(s) 124; inspect device(s) 126; unit of use device(s) 128; automated dispensing device(s) 130; manual fulfillment device(s) 132; review device(s) 134; imaging device(s) 136; cap device(s) 138; accumulation device(s) 140; literature device(s) 141; packing device(s) 142; and unit of use packing device(s) 144. The system 100 may also include additional devices, which may communicate with each other over network 104 or directly.

The order processing device 102 may receive information about prescriptions being filled at a pharmacy in which the order processing device 102 is deployed. In general, the order processing device 102 is a device located within or otherwise associated with a pharmacy location to enable fulfillment of a prescription by dispensing prescription drugs. In some embodiments, the order processing device 102 may be a device separate from a pharmacy that enables communication with other devices located within a pharmacy. For example, the order processing device 102 may be in communication with another order processing device 102 and/or other devices 122-144 located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a prescription order as it is fulfilled. A prescription order may include one or more than one prescription to be filled by the pharmacy. The order processing device 102 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 102 may operate in combination with the benefit manager device 106. The order processing device 102 may track and/or schedule the literature or other paperwork associated with each order or multiple prescription orders that are being shipped together.

Examples of the order processing device 102 include a set-top box (STB), a receiver card, a mobile telephone, a personal digital assistant (PDA), a display device, a portable gaming unit, a tablet, and a computing system; however other devices may also be used. For example, the order processing device 102 may include a mobile electronic device, such an IPHONE or IPAD device by Apple, Inc., mobile electronic devices powered by ANDROID by Google, Inc., and a BLACKBERRY device by Blackberry Limited. The order processing device 102 may also include other computing devices, such as desktop computing devices, notebook computing devices, netbook computing devices, gaming devices, servers, and the like. The device 102 may include circuitry, a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for creation and/or management of the pharmacy or drug benefit. While this benefit manager operating the benefit manager device 106 is typically a pharmacy benefit manager (PBM), other entities may operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, or otherwise.

Some of the operations of the PBM that operates the benefit manager device 106 may include the following. A member (or a person on behalf of the member) of a pharmacy benefit plan administered by or through the PBM attempts to obtain a prescription drug at a retail pharmacy location where the member can obtain drugs in a physical store from a pharmacist or pharmacist technician, or in some instances through mail order drug delivery from a mail order pharmacy location. The member may also obtain a prescription drug directly or indirectly through the use of a machine, such as a kiosk, vending unit, mobile electronic device, or a different type of mechanical, electrical, electronic communication device and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of a plan sponsor or client with the PBM. The member's co-pay may be based on a flat co-pay (e.g., $10), co-insurance (e.g., 10%), and/or a deductible (e.g., for first $500 of annual prescription drug spend) for certain prescription drugs, certain types and/or classes of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. The co-pay may also vary based on the delivery channel used to receive the prescription drug. For example, the co-pay for receiving prescription drug from a mail order pharmacy location may be less than the co-pay for receiving prescription drug from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing an applicable formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 106 and/or an additional device.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage) and/or through the network 104 (e.g., in a cloud configuration or software as a service) with a database 108 (e.g., as may be retained in memory or otherwise). The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high volume fulfillment center to fulfill a pharmacy order.

In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the prescription container (e.g., a prescription bottle and sealing lid) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets used to transport prescriptions within the pharmacy may also be stored as order data 110.

The member data 112 includes information regarding the members associated with the benefit manager. The information stored as member data 112 may include personal information, personal health information, protected health information, and the like. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, e.g., the high volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data 112, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of devices 122-144, recited above. In some embodiments, operations performed by one of these devices 122-144 may be performed sequentially, or in parallel with the operations of another device as may be coordinated by the order processing device 102. In some embodiments, the order processing device 102 tracks a prescription with the pharmacy based on operations performed by one or more of the devices 122-144.

In some embodiments, the system 100 may transport prescription drug containers (e.g., between one or more than one of the devices 122-144 in the high volume fulfillment center) by use of pallets. The pallet sizing and pucking device 122 may configure pucks in a pallet. A pallet may be a transport structure for a number of prescription containers, and may include a number of cavities. A puck may be placed in one or more than one of the cavities in a pallet by the pallet sizing and pucking device 122. A puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 102 based on prescriptions which the order processing device 102 decides to launch. In general, prescription orders in the order database 110 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet.

The loading device 124 may load prescription containers into the pucks on a pallet by a robotic arm, a pick and place mechanism, or the like. In one embodiment, the loading device 108 has robotic arms or pickers to grasp a prescription container and move it to and from a pallet or a puck. The loading device 124 may also print a label which is appropriate for a container that is to be loaded onto the pallet, and apply the label to the container. The pallet may be located on a conveyor assembly during these operations, e.g., at the high volume fulfillment center.

The inspect device 126 may verify that containers in a pallet are correctly labeled and in the correct spot on the pallet. The inspect device 126 may scan the label on one or more than one container on the pallet. Labels of containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit of use device 128 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like. Prescription drug products dispensed by the unit of use device 128 may be packaged individually or collectively for shipping, or may be shipped in combination with other prescription drugs dispensed by other devices in the high volume fulfillment center.

The automated dispensing device 130 may include one or more than one devices that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack. Prescription drugs dispensed by the automated dispensing devices 130 may be packaged individually or collectively for shipping, or may be shipped in combination with other prescription drugs dispenses by other devices in the high volume fulfillment center.

The manual fulfillment device 132 may provide for manually fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100 to be joined with other containers in a prescription order for a patient or member. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example, the manual review can be performed at the manual station.

The imaging device 136 may image containers once they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap, although this process may be performed by a subsequent device in the high volume fulfillment center.

The accumulation device 140 accumulates various containers of prescription drugs in a prescription order. The accumulation device 140 may accumulate prescription containers from various devices or areas of the pharmacy. For example, the accumulation device 140 may accumulate prescription containers from the unit of use device 128, the automated dispensing device 130, the manual fulfillment device 132, and the review device 134, at the high volume fulfillment center. The accumulation device 140 may be used to group the prescription containers prior to shipment to the member or otherwise.

The literature device 141 prints, or otherwise generates, literature to include with prescription drug orders. The literature may be printed on multiple sheets of substrates, such as paper, coated paper, printable polymers, or combinations thereof. The literature printed by the literature device 141 may include information required to accompany the prescription drugs included in a prescription order, relating to prescription drugs in the order, financial information associated with the order (e.g., an invoice or an account statement), or the like.

In some embodiments, the literature device 141 folds or otherwise prepares the literature for inclusion with a prescription drug order (e.g., in a shipping container). In some embodiments, the literature device 141 that prints the literature may be separate from the literature device that prepares the literature for inclusion with a prescription order.

The packing device 142 packages a prescription order in preparation for shipping the order. The packing device 142 may box, bag, or otherwise package the fulfilled prescription order for delivery. The packing device 142 may further place inserts, e.g., literature or other papers, into the packaging received from the literature device 141 or otherwise. For example, bulk prescription orders may be shipped in a box, while other prescription orders may be shipped in a bag which may be a wrap seal bag. The packing device 142 may label the box or bag with the address and a recipient's name. The label may be printed and affixed to the bag or box, be printed directly onto the bag or box, or otherwise associated with the bag or box. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The ultimate package may then be shipped through postal mail, through a mail order delivery service that ships via group and/or air (e.g., UPS, FEDEX, or DHL), through delivery service, through a locker box at a shipping site (e.g., AMAZON locker or a PO Box), or otherwise.

The unit of use packing device 144 packages a unit of use prescription order in preparation for shipping the order. The unit of use packing device 144 may include manual scanning of containers to be bagged for shipping to verify each container in the order. In an example embodiment, the manual scanning may be performed at a manual station.

While the system 100 in FIG. 1 is shown to include single devices 102, 106, 122-144 multiple devices may be used. The devices 102, 106, 122-144 may be the same type or model of device or may be different device types or models. When multiple devices are present, the multiple devices may be of the same device type or models or may be a different device type or model. The types of devices 102, 106, 122-144 shown in FIG. 1 are example devices. In other configurations of the system 100, lesser, additional, or different types of devices may be included.

Moreover, the system 100 shows a single network 104; however, multiple networks can be used. The multiple networks may communicate in series with each other to link the devices 102, 106, 122-144 or in parallel to link the devices 102, 106, 122-144. Multiple devices may share processing and/or memory resources. The devices 102, 106, 122-144 may be located in the same area or in different locations. For example, the devices 102, 106, 122-144 may be located in a building or set of adjoining buildings. The devices 102, 106, 122-144 may be interconnected (e.g. by conveyors), networked, and/or otherwise in contact with one another or integrated with one another, e.g., at the high volume fulfillment center. In addition, the functionality of a device may be split among a number of discrete devices and/or combined with other devices.

Figure 2:
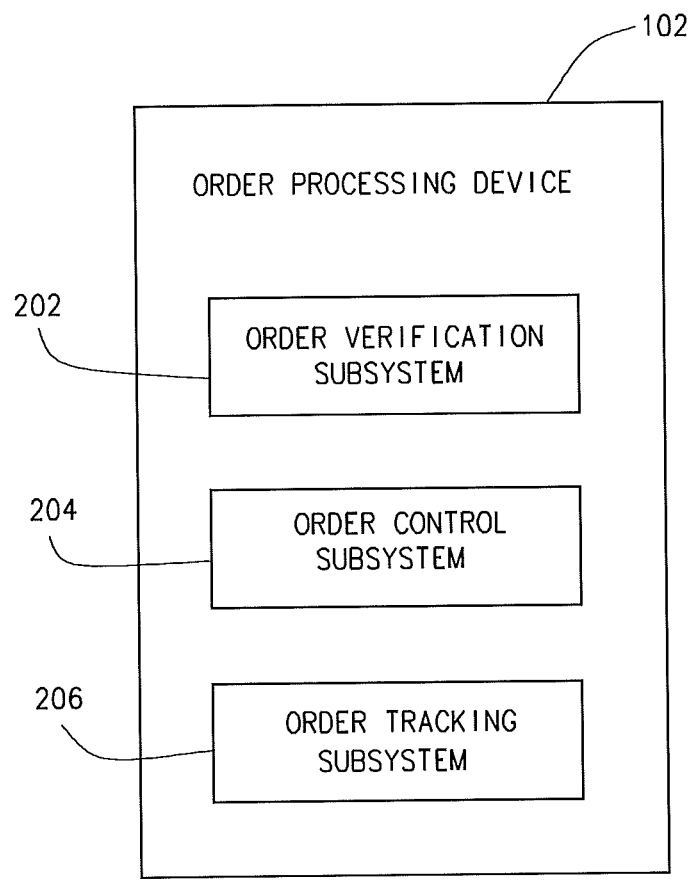
FIG. 2 is a block diagram of an example order processing device that may be deployed within the system of FIG. 1, according to an example embodiment.

FIG. 2 illustrates the order processing device 102, according to an example embodiment. The order processing device 102 may be used by one or more than one operator to generate prescription orders, make routing decisions, make prescription order consolidation decisions, track literature with the system 100, and/or view order status and other order related information. For example, the prescription order may be comprised of order components. The order processing device 102 may receive instructions to fulfill an order without operator intervention. An order component may include a prescription drug fulfilled by use of a container through the system 100. The order processing device 102 may direct an order component to the manual fulfillment device 132 and/or to the review device 134, and direct other components to the automated dispensing device 130. The order processing device 102 may direct order components to the accumulation device 140 for aggregation before shipping. The order processing device 102 may direct the order components directly to the packing device 142 if the prescription order does not require accumulation from various areas of the pharmacy for completion. The order processing device 102 may be deployed in the system 100, or may otherwise be used.

The order processing device 102 may include an order verification subsystem 202, an order control subsystem 204, and/or an order tracking subsystem 206. Other subsystems may also be included in the order processing device 102.

The order verification subsystem 202 may communicate with the benefit manager device 106 to, verify the eligibility of the member, review the formulary to determine appropriate co-pay, coinsurance, and deductible for the prescription drug, and/or perform a DUR. Other communications between the order verification subsystem 202 and the benefit manager device 106 may be performed for a variety of purposes.

The order control subsystem 204 controls various movements of the containers and/or pallets along with various filling functions during their progression through the system 100. In some embodiments, the order control subsystem 204 may identify the prescribed drug in one or more than one prescription order as capable of being fulfilled by the automated dispensing device 130. The order control subsystem 204 may determine which prescriptions are to be launched, and may determine that a pallet of automated-fill containers is to be launched. The order control subsystem 204 may determine that an automated-fill prescription of a specific pharmaceutical is to be launched, and may examine a queue of orders awaiting fulfillment for other prescription orders which will be filled with the same pharmaceutical. The order control subsystem 204 may then launch orders with similar automated-fill pharmaceutical needs together in a pallet to the automated dispensing device 130. As the devices 122-144 may be interconnected by a system of conveyors or other container movement systems, the order control subsystem 204 may control various conveyors to deliver the pallet from the loading device 124 to the manual fulfillment device 132, for example, and the literature device 141 to deliver paperwork as needed to fill the prescription, for example.

The order tracking subsystem 206 may track a prescription order as it progresses (or stops) toward fulfillment. The order tracking subsystem 206 may track, record and/or update order history, order status, or the like. The order tracking subsystem 206 may store data locally (e.g., in a memory) or as a portion of the order data 110 stored in the database 108.

Figure 3:
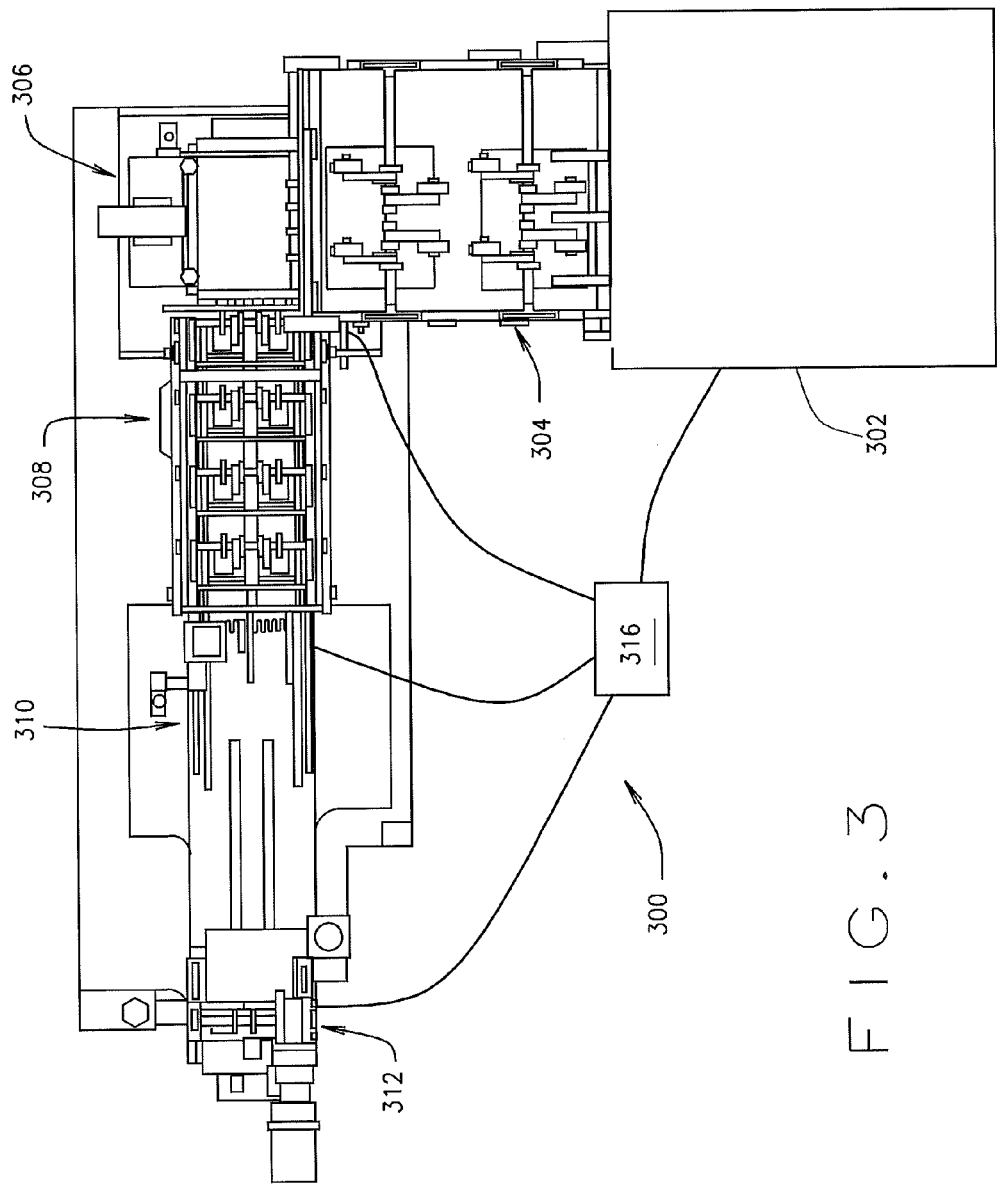
FIG. 3 is a top plan view of a paper feed device, according to an example embodiment.
Figure 4:
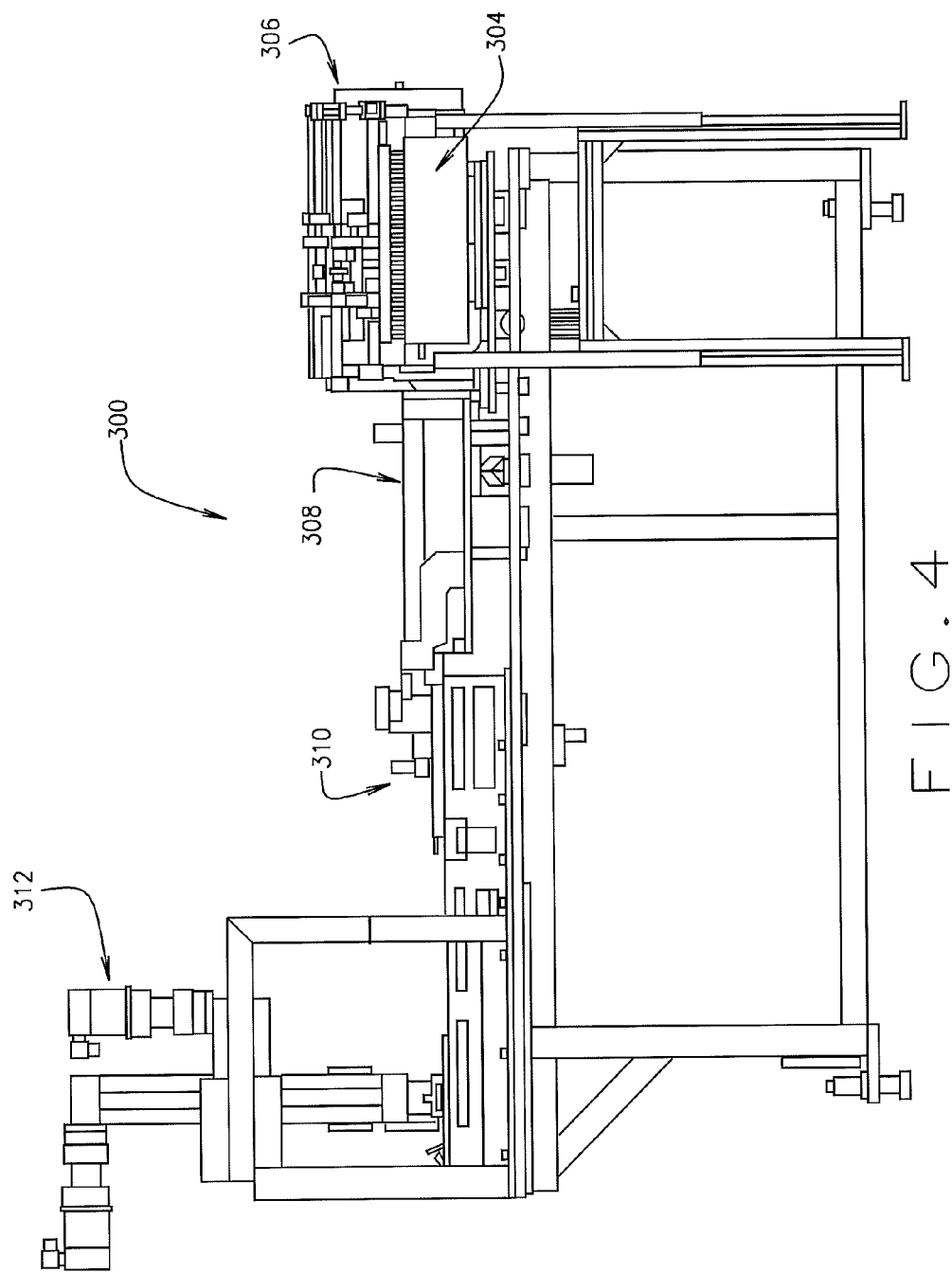
FIG. 4 is side view of a paper feed device, according to an example embodiment.

FIGS. 3 and 4 illustrate views of an example paper feed device 300, according to an example embodiment. The paper feed device 300 may be deployed in the system 100 as a literature device 141. Other types of devices beyond the paper feed device 141 may be included with the system 100 as being part of the literature devices 141.

The paper feed device 300 enables management of printed literature between printing and packaging at packing device 142 or unit of use packing device 144. Printed literature may, as a non-limiting example, contain one or more than one of order data 110, member data 112, claims data 114, drug data 116, prescription data 118, and plan sponsor data 120, and may be included with a prescription order upon shipment to a customer. The printed literature may include single sheets of paper and multiple sheets of paper. A printer 302 may be a component of paper feed device 300, or may be a separate component which merely prints and feeds paper to the paper feed device 300. The paper feed device 300 may also include a paper feed conveyor 304, a paper collator 306, a roller transport 308, a paper stage fixture 310, a robot arm 312, and a control unit 316. The paper feed conveyor 304 feeds printed literature from the printer 302 to the paper collator 306. The paper collator 306 collates printed literature and pulls one or more than one sheet of printed literature for inclusion with a designated prescription order. The robotic arm 312 picks paperwork from the paper stage fixture 310 for placement with a prescription order in a box or bag for shipment to a customer (e.g., a member). The control unit 316 may be deployed in the paper feed device 300, or may otherwise be used. The control unit 316 may operate at the direction of the order processing device 102, or may be integral with the order processing device 102 or otherwise. The control unit 316 may include circuitry, processors, and like hardware to execute instructions and memory to store order data and instructions.

The paper fixture stage 310 shown in FIGS. 3 and 4 is an unfolded paper fixture stage 310. It is noted that a folded paper fixture stage 314 (as illustrated in detail in FIGS. 10-11) may be implemented instead of or in addition to the unfolded paper fixture stage 310. In an example embodiment, when a set of printed literature to be included with a prescription order is less than 15 pages, the folded paper fixture stage 314 is used to fold the complete set of printed literature in half before placement with the prescription order for shipment. However, when a set of printed literature to be included with a prescription order is 15 pages or more, the unfolded paper fixture stage 310 is used and the printed literature remains unfolded. The actual threshold number of pages that trigger a folded/unfolded decision may be changed as desired.

The printer 302 may be a high volume printer capable of printing approximately 100-150 sheets per minute (50-75 pages per minute in duplex mode). The control unit 316 may be in communication with the printer 302 to initiate printing of literature for a selected prescription order once the fulfillment of the prescription order has reached a certain point or stage within the pharmacy. As a non-limiting example, the order processing device 102 or the control unit 316 may determine that the fulfillment of a prescription order is complete and ready for shipment. Such a determination may occur once one or more than one pharmaceutical containers filled with pharmaceuticals according to the prescription order are scanned upon arrival at the accumulation device 140. At that time, the control unit 316 may instruct the printer 302 to print the literature which is associated with the prescription order, so that the printed literature and pharmaceutical containers can be gathered for shipment at the packing device 142 or the unit of use packing device 144. In another example, the printer 302 is instructed to print the literature when the prescription order is verified.

Figure 5:
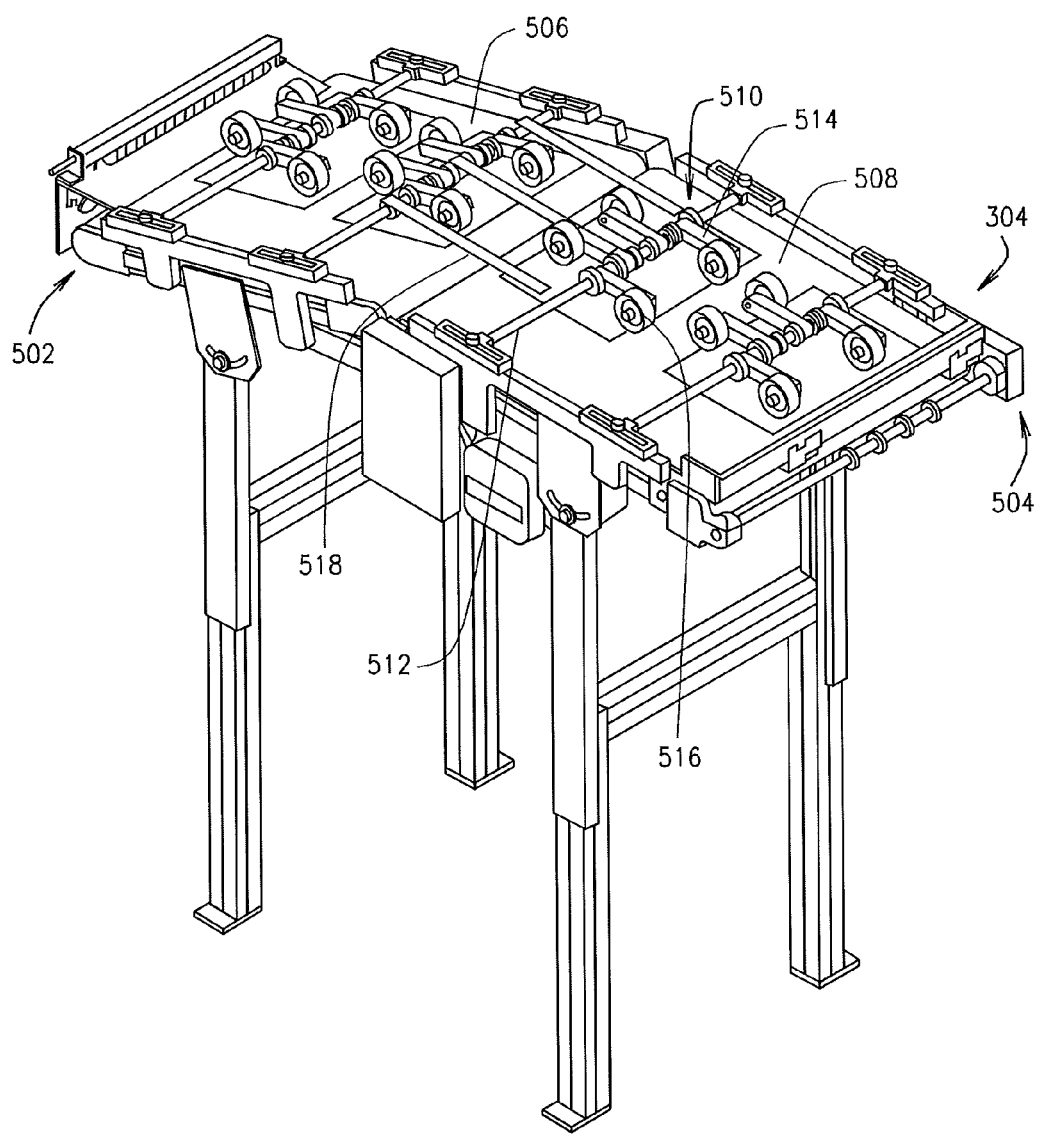
FIG. 5 is a perspective view of a paper feed conveyor, according to an example embodiment.

FIG. 5 illustrates an example embodiment of paper feed conveyor 304. The paper feed conveyor 304 may include a printer end 502 which receives printed pages from the printer 302, as well as a collator end 504 which deposits printed pages into the paper collator 306. The paper feed conveyor 304 may also include a first conveyor belt 506 and a second conveyor belt 508, although more or fewer conveyor belts may instead be used. In some embodiments, a different conveyance mechanism such as rollers maybe used. As shown in FIG. 5, the conveyor belts 506, 508 convey printed literature from the printer 302 to the paper collator 306.

One or more than one wheel devices 510 may be positioned above the conveyor belts 506, 508. As shown in FIG. 5, the wheel device 510 may include a support bar 512, and one or more than one wheel supports 514 may extend off of each support bar 512. At least one wheel 516 may be rotatably connected to each wheel support 514. As shown, two wheel 516/wheel supports/514 combinations extend off of each side of each support bar 512. The wheels 516 may be positioned in contact with or immediately adjacent to a conveyor belt 506, 508. The wheels 516 thereby allow sheets of printed literature to pass thereunder, while assisting in retaining the sheets on the conveyor belt 506, 508. Similarly, one or more than one arms 518 may extend off of a support bar 512 in the direction of travel of the conveyor belts 506, 508. As shown in FIG. 5, the arms 518 are shown extending over the junction between first and second conveyor belts 506, 508 to assist in the transition of sheets of printed literature from the conveyor belt 506 to the conveyor belt 508. The paper feed conveyor 304, the roller transport 308, and a robot 312 are non-limiting examples of paper conveyance mechanisms. Other types of paper conveyance mechanism may be used in place of or in addition to the paper feed conveyor 304, the roller transport 308, and the paper conveyance mechanism.

Figure 6:
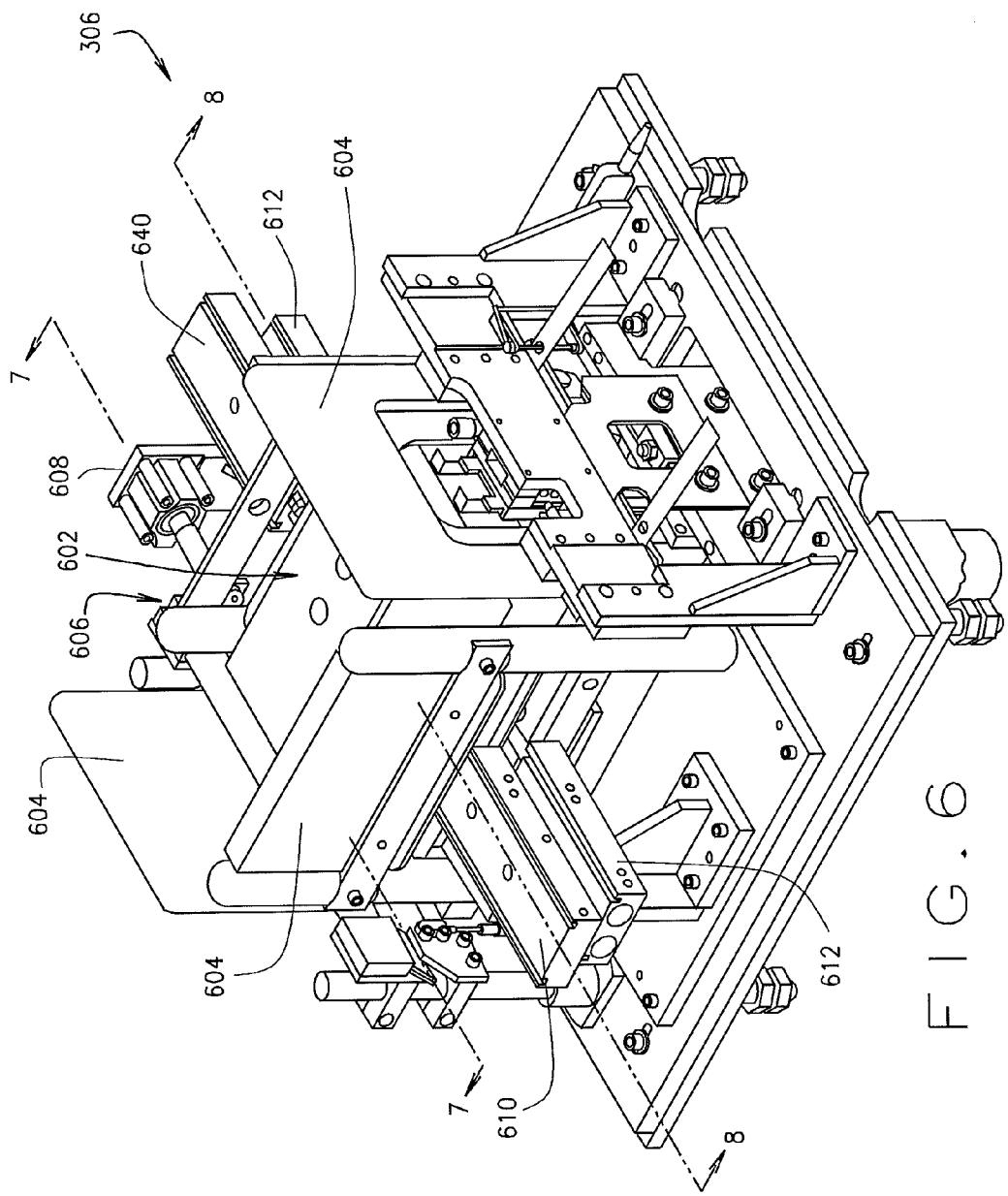
FIG. 6 is a perspective view of a paper collator, according to an example embodiment.
Figure 7:
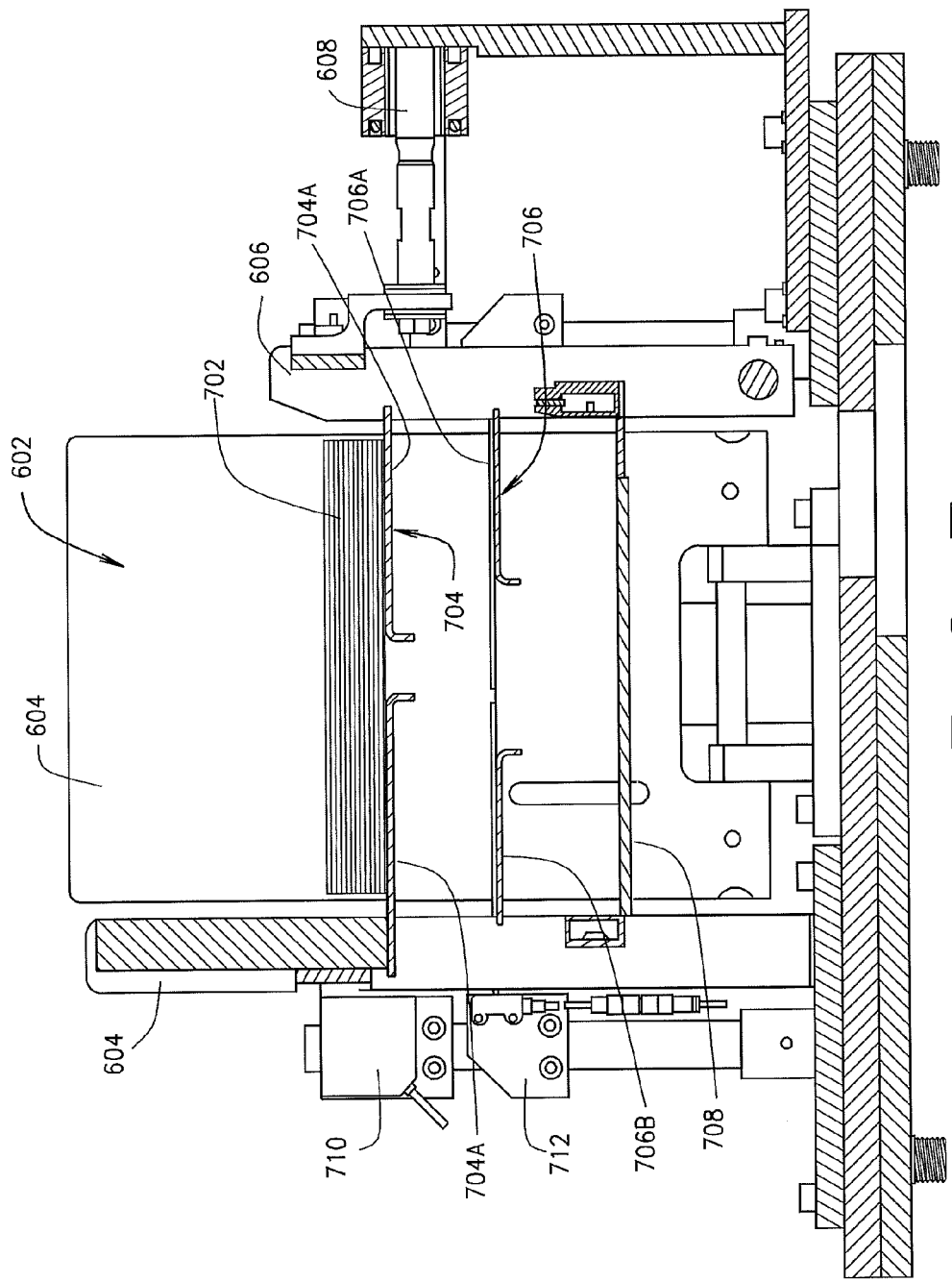
FIG. 7 is a cross-sectional view of a paper collator, according to an example embodiment.
Figure 8:
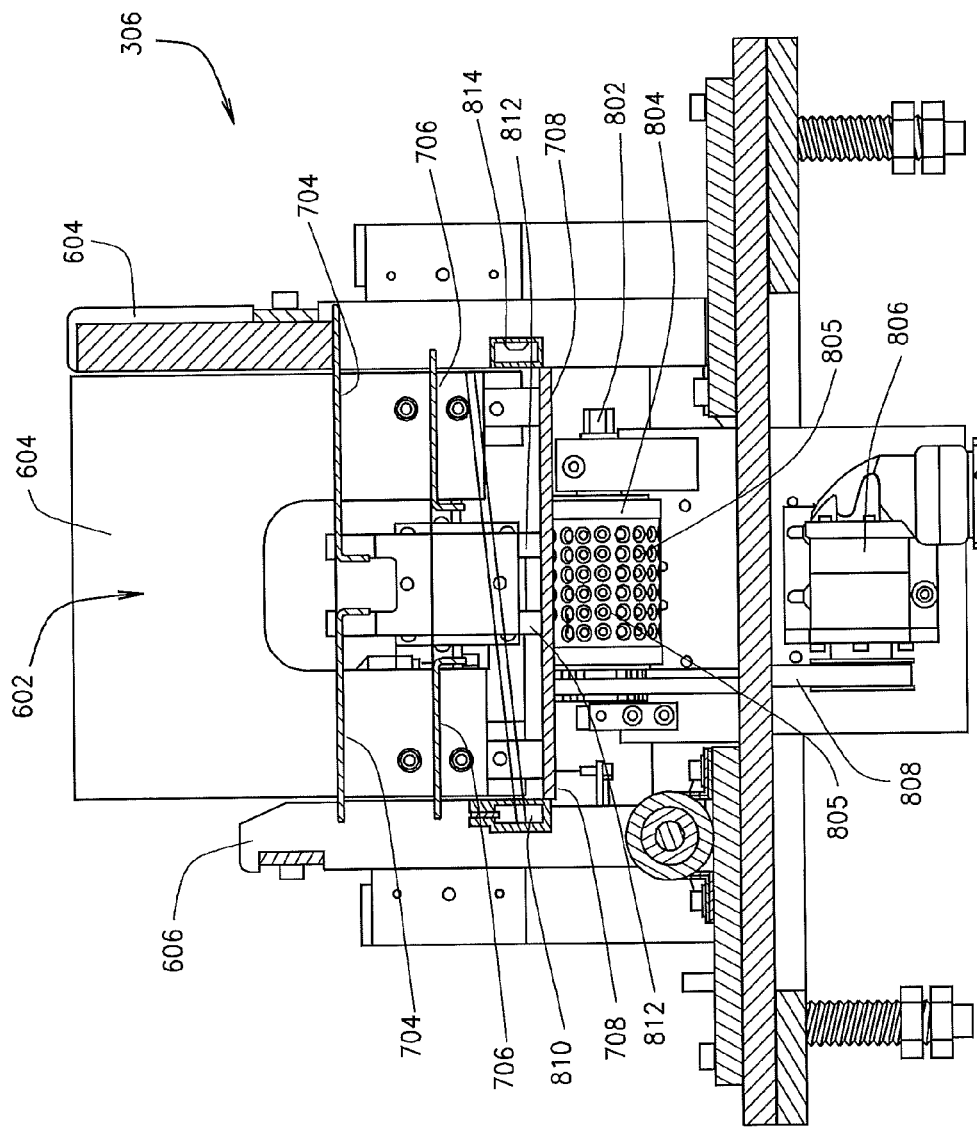
FIG. 8 is an cross-sectional view of a paper collator, according to an example embodiment.

FIGS. 6-8 illustrate various views of an example embodiment of the paper collator 306. As can be seen in FIG. 6, paper collator 306 may include a paper containment area 602 into which printed literature is deposited by paper feed conveyor 304. Paper containment area 602 may be formed on three sides by walls 604. In an example embodiment, such as that shown in FIG. 6, one or more than one bumper post 606 may be positioned on at least one side of the paper containment area 602. An actuator 608 may be connected to the bumper post 606 to cause movement of the bumper post 606 slightly into and out of the paper containment area 602. The post 606 may include multiple vertically elongated bodies that are horizontally spaced. Such action may be used to bump and align printed literature that is deposited by the paper feed conveyor 304 into the paper collator 306. One or more than one upper linear actuator 610 and lower linear actuator 612 are also visible in FIG. 6.

FIGS. 7 and 8 illustrate cross sectional views of the paper collator 306, looking in opposite directions from one another. As can be seen in FIG. 7, two walls 604 are visible, along with a bumper post 606 and an actuator 608. In addition, a stack of pages of printed literature 702 is seen resting on top of an upper shelf 704. Below the upper shelf 704 is a middle shelf 706, and the below middle shelf 706 is a lower shelf 708. As illustrated in FIGS. 7 and 8, the upper shelf 704 may be formed by separate shelf panels 704A and 704B. Each shelf panel 704A, 704B may be connected to an upper linear actuator 610, illustrated in FIG. 6. Actuation of the upper linear actuators 610 causes the shelf panels 704A, 704B to be pulled outwardly (toward walls), allowing a stack of printed literature 702 to drop to the middle shelf 706. Upper linear actuators 610 may then force shelf panels 704A, 704B inwardly so that a new stack of printed literature 702 may be stacked thereon. More or fewer shelf panels may be used to form the upper shelf 704, as would be understood.

The middle shelf 706 may also be formed by separate shelf panels 706A and 706B. Each shelf panel 706A, 706B may be connected to a lower linear actuator 612, illustrated in FIG. 6. Actuation of the lower linear actuators 612 causes the middle shelf panels 706A, 706B to be pulled outwardly, allowing a stack of printed literature 702 to drop to the lower shelf 708. The lower linear actuators 612 may then force the shelf panels 706A, 706B inwardly so that a new stack of printed literature 702 may be stacked thereon. More or fewer shelf panels may be used to form middle shelf 706.

The control unit 316 may control the linear actuators 610, 612. Additionally, as shown in FIG. 7, an upper sensor 710 and a middle sensor 712 may be in communication with the control unit 316. The upper and middle sensors 710, 712 may be laser sensors or other types of sensors. The upper and middle sensors 710, 712 may determine that a stack of printed literature 702 has reached a certain height, or may detect individual pages of printed literature to track the total number of pages of printed literature which are present on a respective shelf. The control unit 316 may thereby determine when to cause the actuation of the upper or lower linear actuators 610, 612 to cause a stack of printed literature 702 to drop to the next lowest shelf 706, 708.

The bumper post 606 may be elongate so that it extends from the bottom shelf 708, past the middle shelf 706 to the upper shelf 704, The bumper post 606 may contact stacks of literature 702 on any or all of the shelves 704, 706 708.

As can be seen in FIG. 8, in an example embodiment, beneath the lower shelf 708 may be a plenum 802 connected with a vacuum drum 804. The vacuum drum 804 may include one or more than one suction apertures 805. A motor 806 may be connected to the vacuum drum 804 and/or the plenum 802 via a belt 808, or by a gear, by a chain, or by another structure. The motor 806 may include a blower that runs in reverse to create a vacuum within the plenum 802 and/or the vacuum drum 804. In some embodiments, such a blower may be a separate component from the motor 806. It is noted that the term vacuum is used herein to denote suction, rather than the presence of a true vacuum, as would be understood. The blower may create a suction between inside the drum 804 relative to outside the drum 804. A fluffer 810 may be positioned to blow fluff air at a stack of printed literature 702 resting at the lower shelf 708. Such a fluffing action from the fluffer 810 may assist in separating a lowest printed material in the stack from adjacent printed material to allow the drum 804 to engage the lowest printed material and remove it from the bottom of the stack. The lower shelf 708 may include a cutout (not shown) sized and positioned to allow a scanner (not shown) to scan at least a portion of the bottom sheet resting on the lower shelf 708.

The control unit 316 may cause the motor 806 (or a separate blower) to create a vacuum within the plenum 802 and/or the vacuum drum 804, and may cause the vacuum drum 804 to rotate. This may cause a sheet of printed literature to be pulled from the bottom of the stack of printed literature 702 resting on the bottom shelf 708. One or more than one snubber 812 may also be present to prevent more than the bottom sheet from being pulled from the stack of printed literature 702. In an example embodiment, a single snubber 812 may be positioned approximately 0.003-0.004 inches above the bottom shelf 708. Additionally, the fluffer 810 may blow fluff air at the stack of printed literature 702 resting on the lower shelf 708 as the bottom sheet from stack 702 is pulled away by the vacuum drum 804. The fluff air may help to lift, separate or fluff sheets of stack of printed literature 702 so that there is less friction to retain the bottom sheet in place. A sensor 814, which may be similar to sensors 710, 712, may also be present at the lower shelf 708 to allow the control unit 316 to evaluate the stack of printed literature 702 on the lower shelf 708.

The roller transport 308 may have a similar structure to that of the paper feed conveyor 304. However, just as the paper feed conveyor 304 transports sheets of printed literature from the printer 302 to the paper collator 306, the paper singluator 308 transports sheets of printed literature from the paper collator 306 to the paper fixture stage 310. In some embodiments, the roller transport 308 may include a conveyor belt and/or rollers to transport sheets of product literature. The paper singluator 308 may also include wheel devices and the like.

Figure 9:
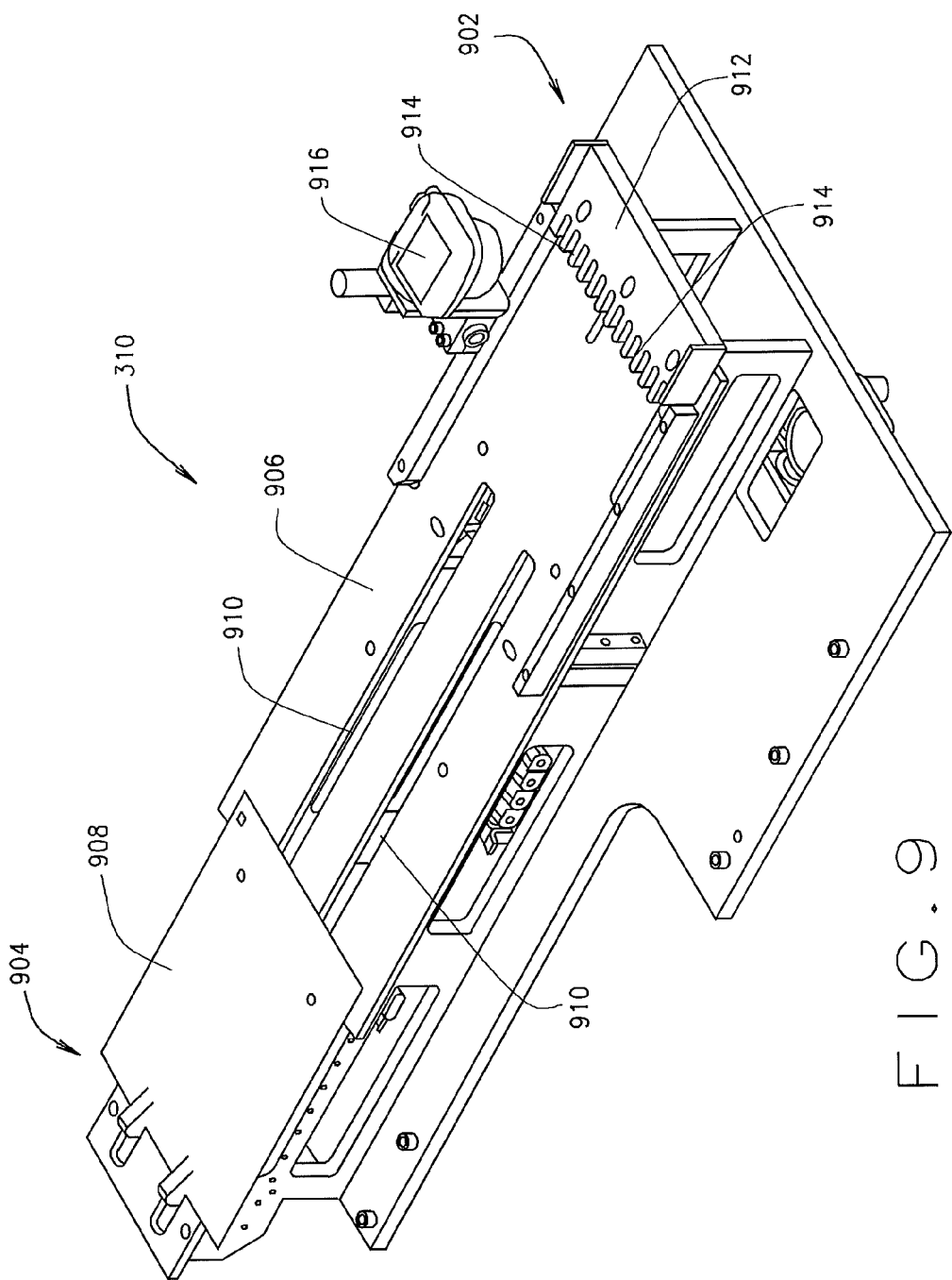
FIG. 9 is a perspective view of a paper handler, according to an example embodiment.
Figure 10:
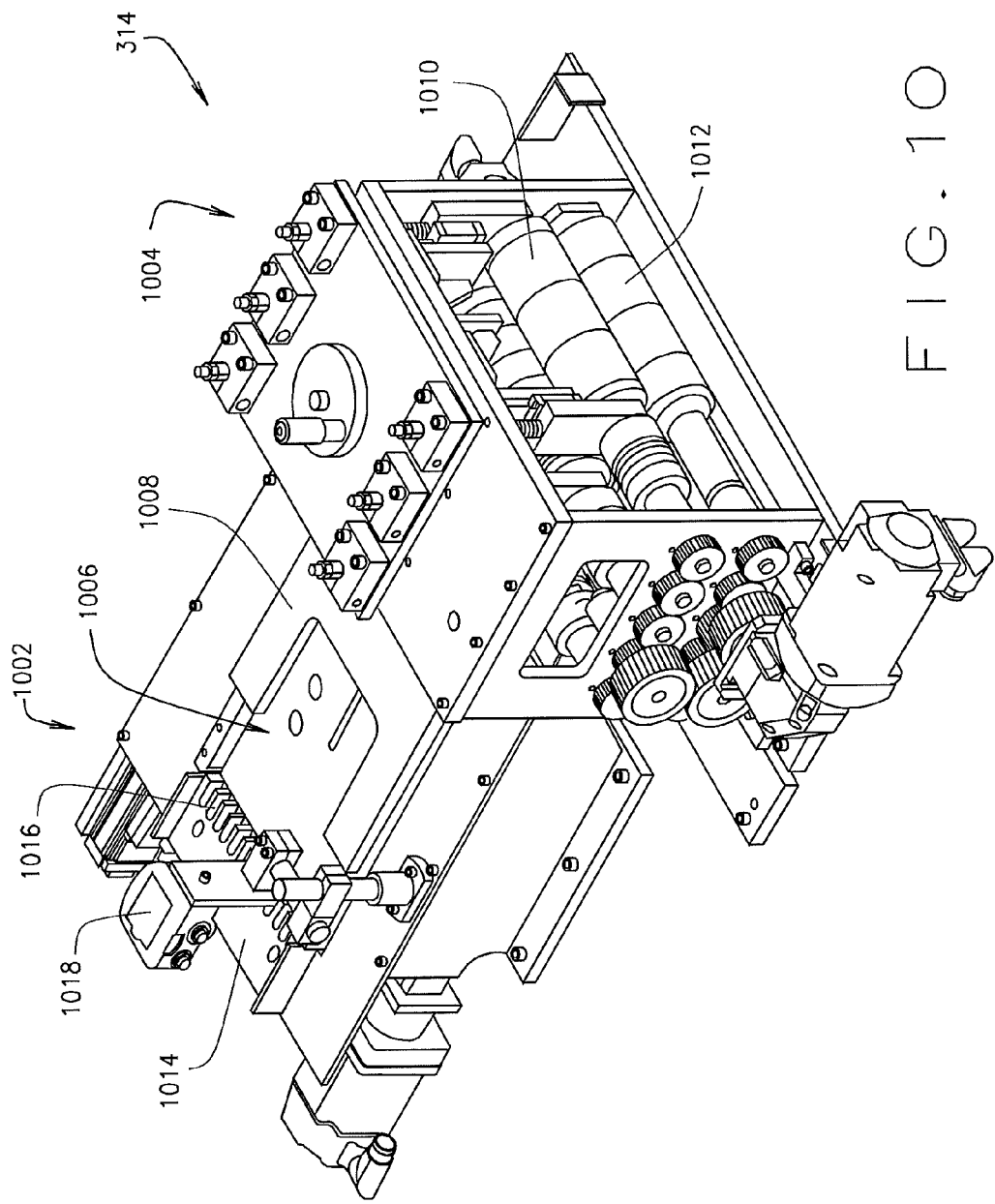
FIG. 10 is a perspective view of a folded paper handler, according to an example embodiment.

FIG. 9 illustrates an example embodiment of a paper fixture stage 310. As noted above, the paper fixture stage 310 is an unfolded stage. FIG. 10, discussed below, illustrates a folded paper fixture stage 314. As shown, the paper fixture stage 310 includes a reception end 902 and a robot end 904. A platform 906 extends generally from the reception end 902 to the robot end 904 of the paper fixture stage 310. A tray 908 is positioned on the platform 906, and is moveable from the reception end 902 to the robot end 904 of the platform 906 along one or more than one tracks 910. When positioned at the reception end 902 of paper fixture stage 310, the tray 908 receives sheets of printed literature from the paper singluator 308. The tray 908 may then be moved to the robot end 904 of the paper fixture stage 310, where the robotic arm 312 may pick up the printed literature from the tray 908. Additionally, at the reception end 902 of the platform 906 may be a comb device 912. The comb device 912 may include multiple tines 914 spaced apart from one another. The spaces between the tines 914 allow sheets of printed literature to settle faster on the tray 908 by giving air underneath such sheets a way to escape.

One or more scanners 916, 918, which may be barcode scanners, are positioned to scan sheets of printed literature. In an example embodiment, the scanners 916, 918 are positioned at the reception end 902 and may scan the literature as it enters the paper fixture stage 310. One or more than one scanner such as the scanners 916, 918 may be present at various points along the paper feed device 300. Such scanners may identify sheets of printed literature as they pass through the paper feed device 300, and may scan both the top and bottom of such sheets. Although one or more than one of the scanners are identified and shown in the FIGS., additional scanners may be positioned and used at other locations along the paper feed device 300. Such scanners may determine the order data 110 and the page number of a given sheet of printed literature, and such information may be encoded via barcode or other encoding system. For example, a scanner such as the scanner 916 may determine that a given sheet of printed literature is page 4 of 7 (or 3 of 7 and 4 of 7, if both sides of the sheet are scanned) associated with a given prescription order. This scanned or determined data may be sent to prescription order tracking devices such as the order processing device 102.

Figure 11:
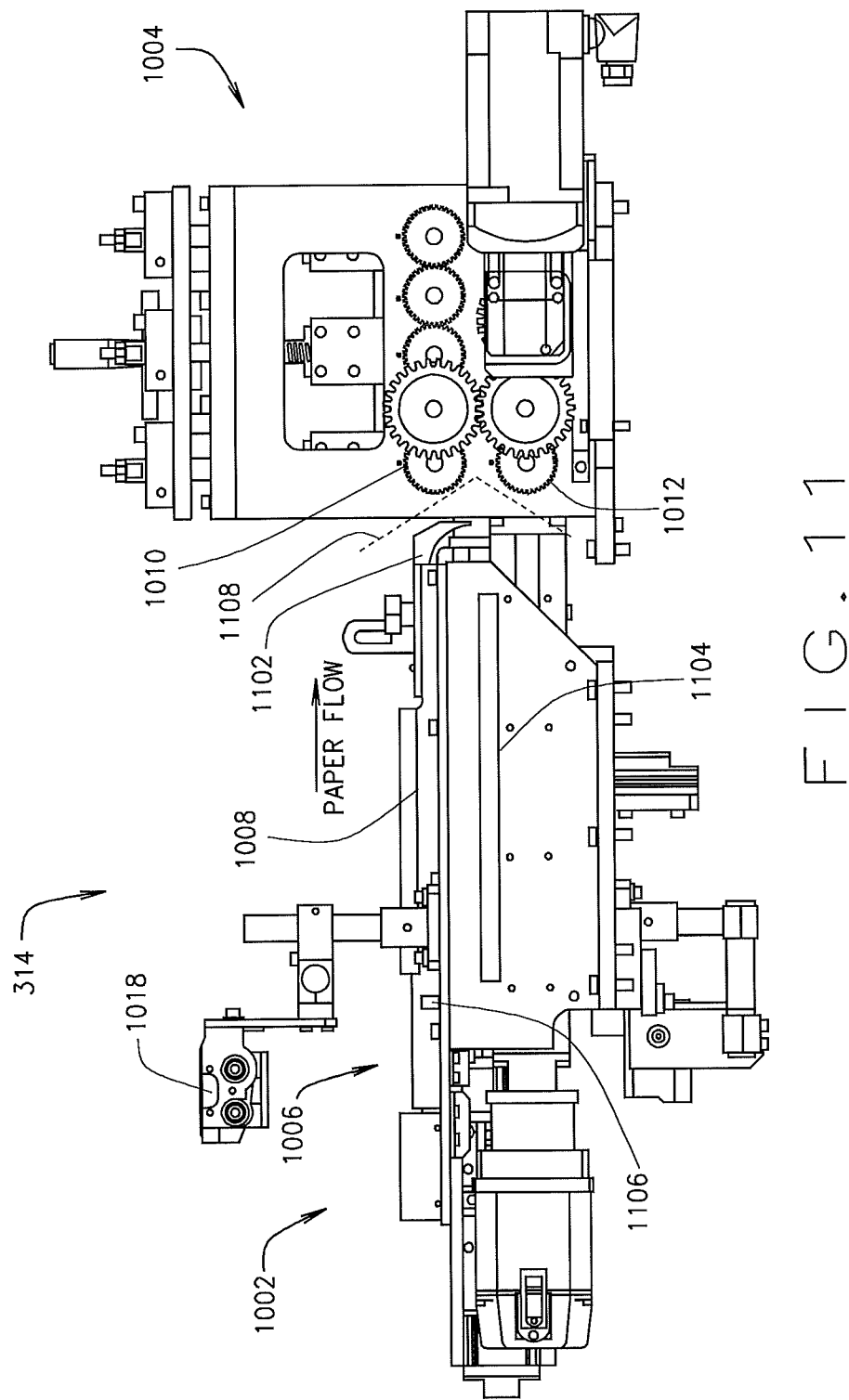
FIG. 11 is a side view of a folded paper handler, according to an example embodiment.

FIGS. 10 and 11 illustrate another example embodiment of a paper fixture stage, this one a folded paper fixture stage 314. As shown in FIG. 10, the folded paper fixture stage 314 includes a reception end 1002 and a folding end 1004. Sheets of printed literature that form the literature for a given order are deposited into a slot 1006 below a guide 1008. As can best be seen in FIG. 11, the guide 1008 includes a curved end portion 1102. The folded paper fixture stage 314 also includes a piston 1104 and one or more than one fingers 1106. The fingers 1106 are selectively moveable in the direction of the curved end portion 1102 of the guide 1008, such that they push sheets of printed literature for a given order toward the curved end portion 1102. The curved end portion 1102 causes the sheets to curve downwardly, at which point the piston 1104 extends and engages the sheets of printed literature at approximately their midpoint to begin making a fold. The piston 1104 then pushes the midpoint of the printed literature sheets between one or more than one upper roller 1010 and one or more lower roller 1012. The upper and lower rollers 1010, 1012 then cause folding of the sheets of printed literature (shown in phantom in FIG. 11 at numeral 1108) with the folded edge being the midpoint that is initially fed into the rollers 1010,1012. The folded sheets of printed literature exit the roller end 1004 of the folded paper fixture stage 314, and are ready for placement by the robotic arm 312. Movement of the fingers 1106 and the piston 1104 may be caused by an actuator or motor, or by another mechanism.

The robotic arm 312 may be a SCARA robot or the like. In an example embodiment, the robotic arm 312 includes arms and linkages that may be driven by actuators or motors to move the arms in any of the X, Y, Z coordinates or in the X, Y coordinates. In an example embodiment, the robotic arm 312 may be adapted to pick the printed literature, either folded or unfolded, and place it with a fulfilled prescription order for shipment. The robotic arm 312 may include or otherwise utilize a scanner to confirm that all sheets associated with an order are accounted for before shipment. Other devices may additionally or alternatively be used to move printed literature from the paper feed device 300 to the packing device 140 or the unit of use packing device 142.

Figure 12:
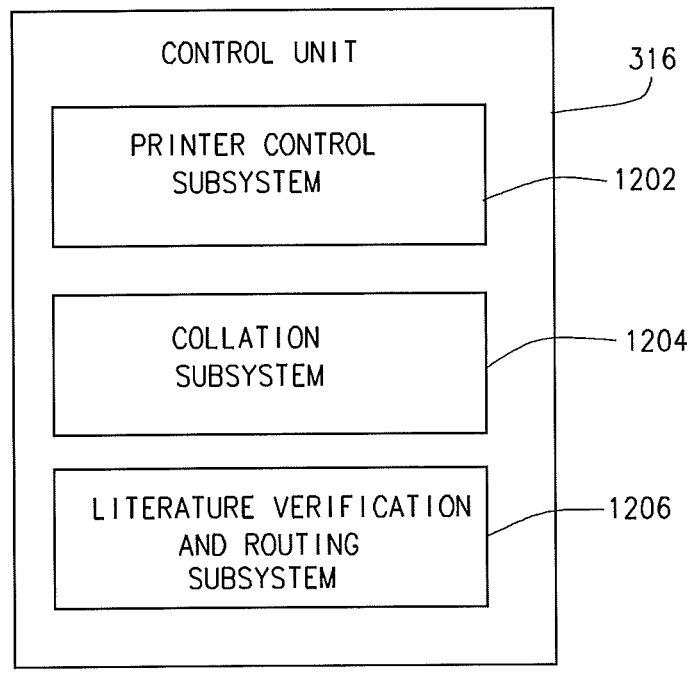
FIG. 12 is a block diagram of a controller, according to an example embodiment.

FIG. 12 illustrates the control unit 314, according to an example embodiment. The control unit 314 may include a printer control subsystem 1202, a collation subsystem 1204, and a literature verification and routing subsystem 1206. Each subsystem may include circuitry, e.g., processors, logic, and memory, to execute instructions on sensed data. The control unit 314 may be responsible for initiating print jobs of printed literature, and may control the progress of such printed literature through the paper collator 306. Additionally, the control unit 314 may verify printed literature as it passes through the paper feed device 300, and route such printed literature accordingly. The control unit 314 may be communicatively coupled to various sensors and scanners of paper feed device 300.

The printer control subsystem 1202 may enable the control unit 302 to determine when literature for a prescription order should be printed in order to for the printed literature to arrive at the packing device 142 or the unit of use packing device 144 to be mated with the corresponding fulfilled prescription order for shipment. The printer control subsystem 1202 may also communicate with the database 108 to access information to be printed in the printed literature, and may be responsible for instructing the printer 302 to hold on further print jobs based on the status of the paper collator 306 and/or status of filling a prescription container, e.g., a manual fill station. The collation subsystem 1204 may monitor sensors within the paper collator 306 to determine the available capacity thereof, and may direct the operation of actuators, fluffers, and the vacuum drum of the paper collator 306. The literature verification and routing subsystem 1206 may communicate with scanners throughout the paper feed device 300 to monitor the location and completeness of printed literature in the paper feed device 300, and may direct the printed literature associated with a prescription order to the folded or unfolded paper fixture stage 314, 308.

Figure 13:
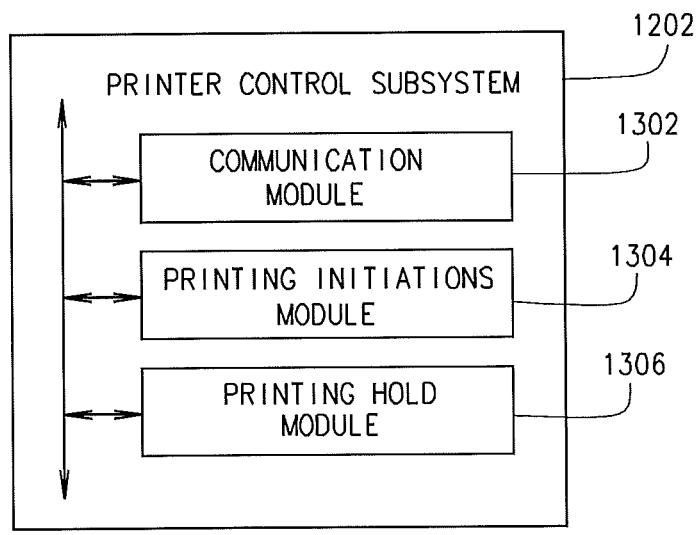
FIG. 13 is a block diagram of a printer controller, according to an example embodiment.

FIG. 13 illustrates an example printer control subsystem 1202 that may be deployed in the control unit 316, or may be otherwise deployed in another system. One or more modules are communicatively coupled and included in the printer control subsystem 1202 to enable the printer control subsystem 1202 to control the printer 302. The modules of the printer control subsystem 1202 that may be included are a communication module 1302, a printing initiation module 1304, and a printing hold module 1306. Other modules may also be included. Each module may include circuitry, e.g., processors, logic, and memory, to execute instructions on sensed data or calculated data.

In some embodiments, the modules of the printer control subsystem 1202 may be distributed so that some of the modules are deployed in other devices within the pharmacy. In one embodiment, the modules are deployed in memory and executed by a processor coupled to the memory. The functionality contained within the modules 13024306 may be combined into a lesser number of modules, further divided among a greater number of modules, or redistributed among existing modules. Other configurations including the functionality of the modules 1302-1306 may be used.

The communication module 1302 may manage communication with, for example, the database 108, the accumulation device 140, the printer 302, paper collator 306, the paper fixture stages 308, 314, and the robot 312. Thereby, the communication module 1302 may receive a signal from the accumulation device 140 that one or more than one filled prescription orders have arrived at the accumulation device 140. It will be understood that the arrival of one or more filled prescription orders at a different component of system 100 may trigger such communication with communication module 1302. The communication module 1302 may then communicate with database 108 to obtain order data 110, member data 112, claims data 114, drug data 116, prescription data 118, as desired for inclusion in printed literature. The printing initiation module 1304 may then instruct the printer 302 to initiate or queue a print job containing such data for eventual shipment to a customer with the fulfilled prescription order. The printing hold module 1306 may communicate with the printer 302 to cause the printer 302 to stop or hold further print jobs, as discussed below in connection with the collation subsystem 1204.

Figure 14:
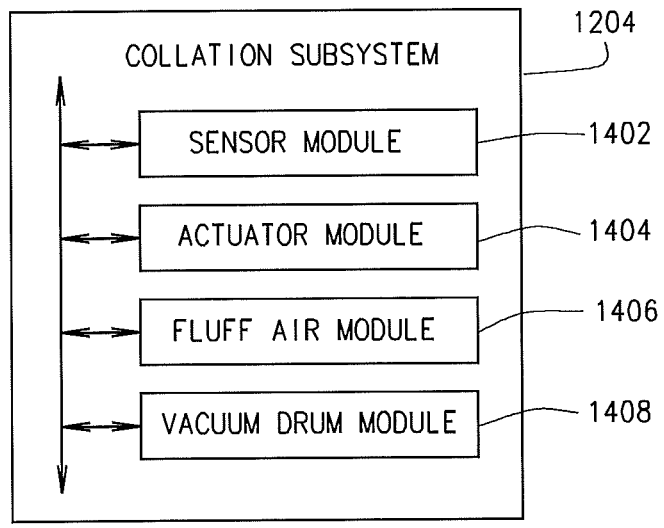
FIG. 14 is a block diagram of a collator, according to an example embodiment.

FIG. 14 illustrates an example collation subsystem 1204 that may be deployed in the control unit 316, or may be otherwise deployed in another system. One or more modules are communicatively coupled and included in the collation subsystem 1204. Each module may include circuitry, e.g., processors, logic, and memory, to execute instructions on sensed data or calculated data. The modules of the collation subsystem 1204 that may be included are a sensor module 1402, an actuator module 1404, a fluff air module 1406, and/or a vacuum drum module 1408. Other modules may also be included.

In some embodiments, the modules of the collation subsystem 1204 may be distributed so that some of the modules are deployed in other devices within the pharmacy. In one embodiment, the modules are deployed in memory and executed by a processor coupled to the memory. The functionality contained within the modules 1402-1408 may be combined into a lesser number of modules, further divided among a greater number of modules, or redistributed among existing modules. Other configurations including the functionality of the modules 1402-1408 may be used.

The sensor module 1402 may be in communication with the sensors 710, 712 to monitor for the presence of printed literature at various stages of the paper collator 306, and to determine additional capacity therein. The actuator module 1404 may cause the upper and lower linear actuators 610, 612 to open and close the upper shelf 704 and the middle shelf 706 to allow printed literature to move through the paper collator 306. The fluff air module 1406 may control the fluffer 810 to expel fluff air directed at printed literature resting on the lower shelf 708. The vacuum drum module 1408 may initiate a suction (e.g., vacuum function) within the vacuum drum 804 and/or the plenum 802, and may cause rotation thereof.

Figure 15:
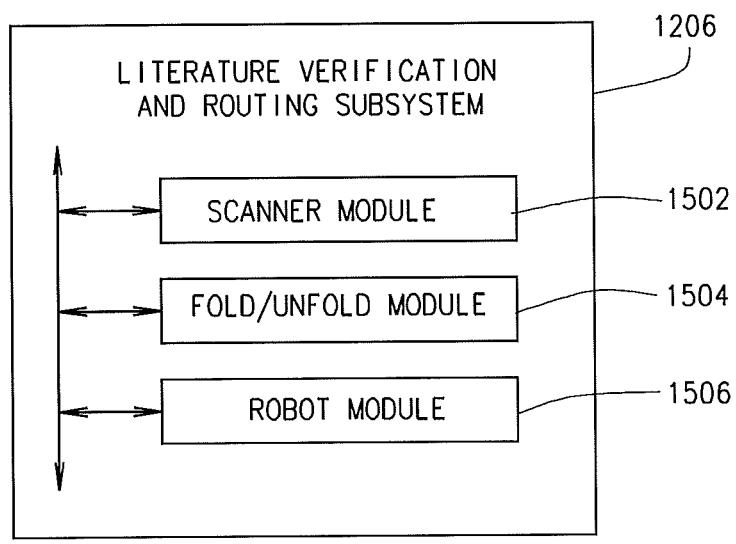
FIG. 15 is a block diagram of a literature-verification and routing subsystem, according to an example embodiment.

FIG. 15 illustrates an example literature verification and routing subsystem 1206 that may be deployed in the control unit 316, or may be otherwise deployed in another system. One or more modules are communicatively coupled and included in the literature verification and routing subsystem 1206. Each module may include circuitry, e.g., processors, logic, and memory, to execute instructions on sensed data or calculated data. The modules of the literature verification and routing subsystem 1204 that may be included are a scanner module 1502, a fold/unfold module 1504, and/or a robot module 1506. Other modules may also be included.

In some embodiments, the modules of the literature verification and routing subsystem 1206 may be distributed so that some of the modules are deployed in other devices within the pharmacy. In one embodiment, the modules are deployed in memory and executed by a processor coupled to the memory. The functionality contained within the modules 1502-1506 may be combined into a lesser number of modules, further divided among a greater number of modules, or redistributed among existing modules. Other configurations including the functionality of the modules 1502-1506 may be used.

The scanner module 1502 may be in communication with scanners, such as the seamier 916 or other scanners located elsewhere in the paper feed device 300 to determine the location and completeness of printed literature in the paper feed device 300. The fold/unfold module 1504 may determine whether a print job associated with a prescription order is routed to the folded or unfolded paper fixture stage 314, 308 based on the number of sheets in the print job. The robot module 1506 may control movement and operation of the robot 312 to pick printed literature from the folded and/or unfolded paper fixture stages 314, 308, and place such literature with the associated prescription order in the packing device 142 and/or the unit of use packing device 144.

Figure 16A:
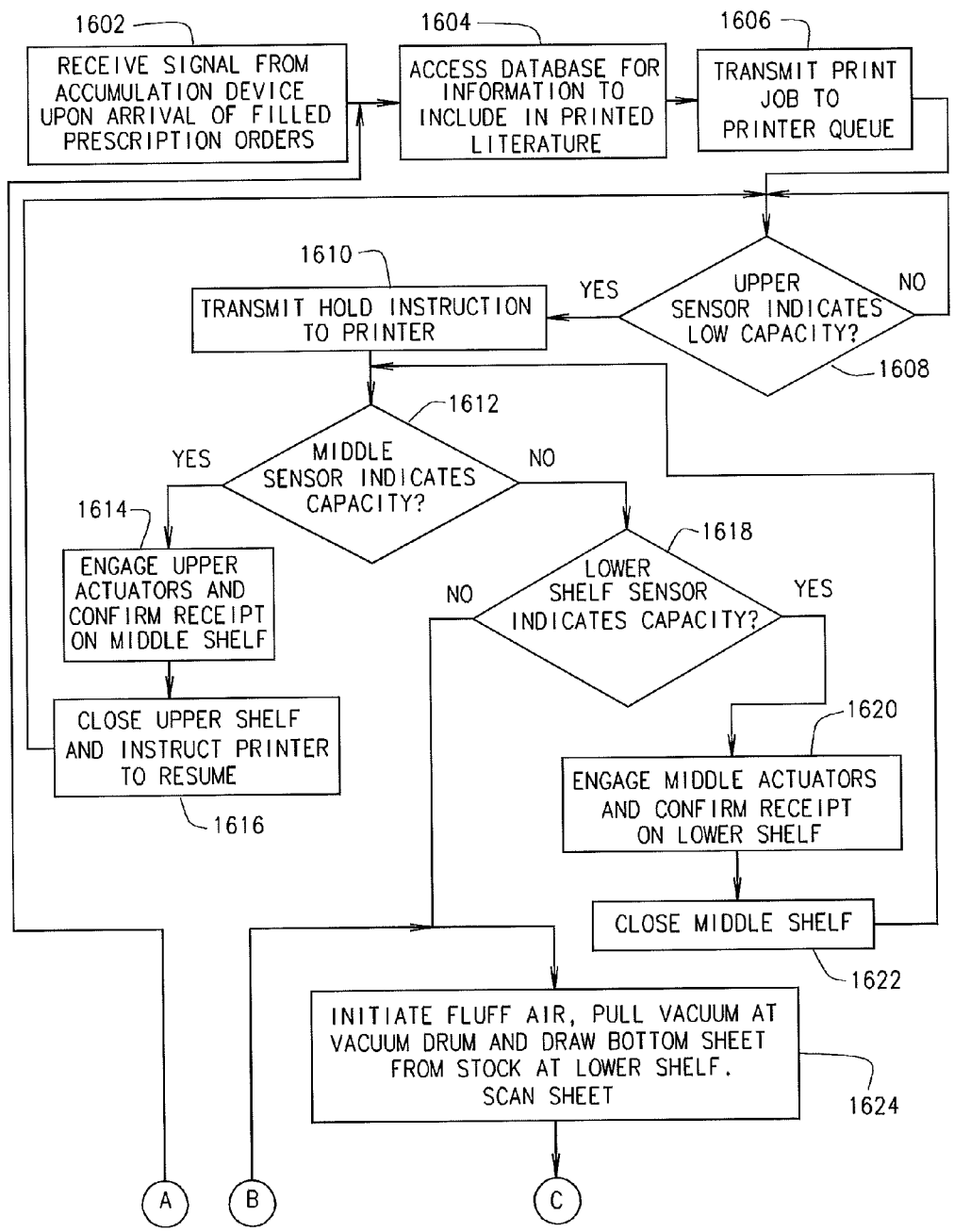
FIGS. 16A and 16B are an example process flow illustrating a method for handling literature for a prescription order, according to an example embodiment.
Figure 16B:
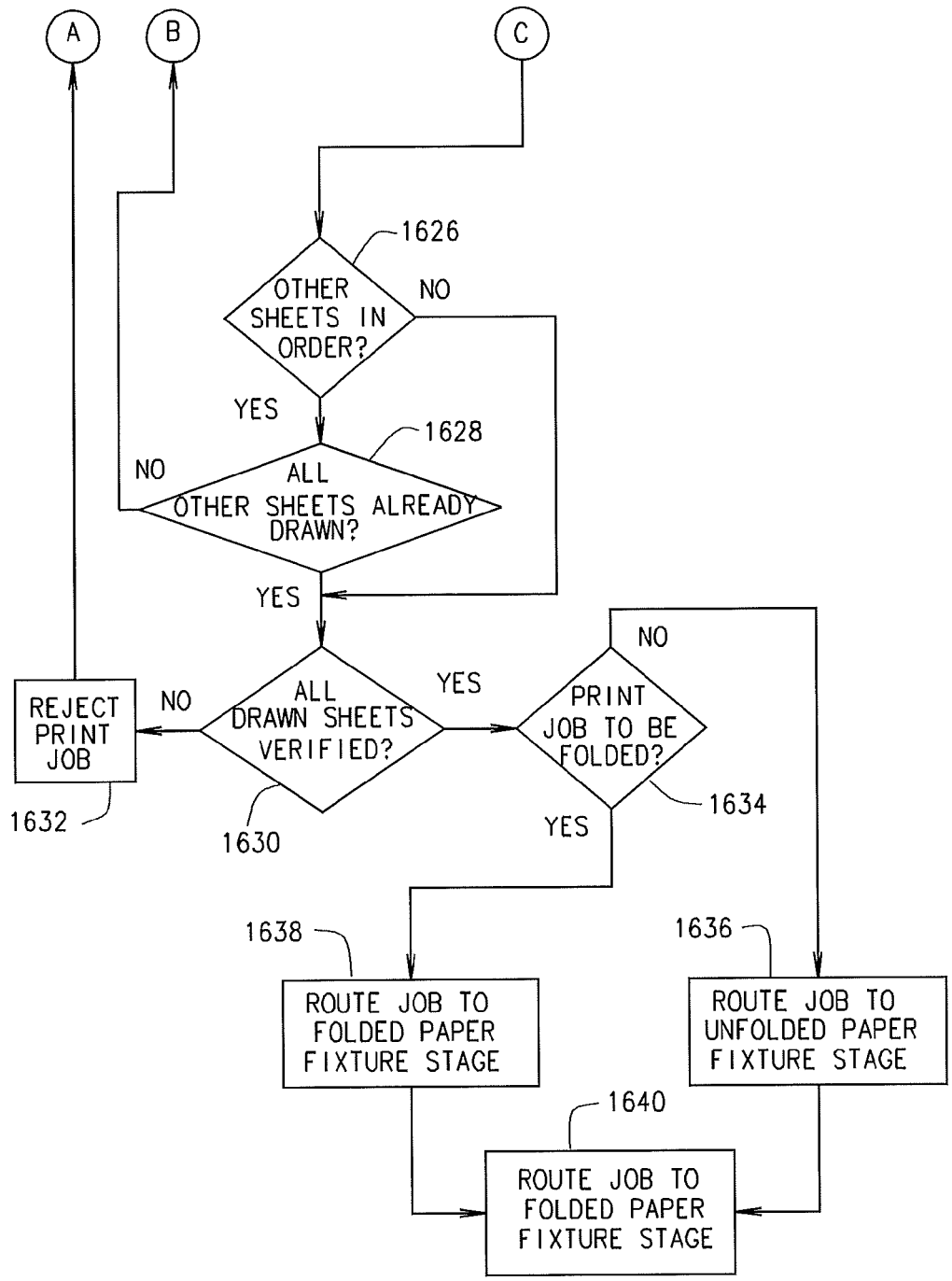

FIGS. 16A and 16B illustrate a method 1600 for printing literature for a prescription order, according to an example embodiment. The method 1600 may be performed by the paper feed device 300 (e.g., as instructed by control unit 316), or may be otherwise performed.

At block 1602, a signal is received regarding the status of the fulfillment of a prescription order. Such a signal may be received from an accumulation device 140 upon arrival of a fulfilled prescription order, or by another device within system 100 at another time. The signal may be received by the communication module 1302 of the control unit 316.

At block 1604, the control device 316 may then utilize the control module 1302 to access a database 108 to obtain one or more of the order data 110, the member data 112, the claims data 114, the drug data 116, and the prescription data 118 for inclusion in printed literature associated with the prescription order. At block 1606, the control unit 316 may then transmit instructions to the printer 302 to queue a print job containing the desired data for the prescription order.

As print jobs are printed by printer 302, the control unit 316 may monitor the capacity of the paper collator 306. At block 1608, the sensor module 1402 of the control unit 316 may communicate with the upper sensor 710 to determine whether the paper collator 306 is nearing capacity at its upper shelf 704. If not, block 1608 repeats until the upper sensor 710 determines that the paper collator 306 is nearing capacity. At that point, the printing hold module 1306 of control unit 316 may transmit a hold instruction to the printer 302 to cease new print jobs at block 1610. The printer 302 may finish printing any print jobs which have already commenced.

At block 1612, the sensor module 1402 may communicate with middle sensor 712 to determine whether the middle shelf 706 has capacity. Where the middle shelf 706 does have capacity, the actuator module 1404 of the control unit 316 may instruct upper linear actuator 610 to open the upper shelf 704 at block 1614. The sensor module 1402 may also confirm with middle sensor 712 that printed literature dropped from the upper shelf 704 has been received by the middle shelf 706. At block 1616, the actuator module 1404 may instruct the upper linear actuator 610 to close the upper shelf 704, and the communication module 1302 may instruct the printer 302 to resume printing.

However, if the middle shelf does not have capacity at block 1612, the sensor module 1402 may communicate with the lower sensor 814 to determine whether the lower shelf 708 has capacity at block 1618. When the lower shelf 708 does have capacity, the actuator module 1404 of the control unit 316 may instruct the lower linear actuator 612 to open the middle shelf 706 at block 1620. The sensor module 1402 may also confirm with the lower sensor 814 that printed literature dropped from the middle shelf 706 has been received by the lower shelf 708. At block 1622, the actuator module 1404 may instruct the lower linear actuator 612 to close the middle shelf 706, and the process may return to block 1612 discussed above.

However, if the lower shelf does not have capacity at block 1618, at block 1624, the vacuum drum module 1408 of the control unit 316 may instruct the vacuum drum 804 and/or the plenum 802 to pull a vacuum and advance to draw the bottom sheet from the stack of printed literature on the bottom shelf 708. Fluff air module 1406 helps the vacuum drum 804 and/or the plenum 802 to draw a single sheet by controlling fluff air blown into the stack of printed literature by fluffer 810. At block 1626, the scanner module 1502 communicates with the scanner 916 to scan the sheet drawn from the stack of printed literature to determine whether there are other sheets associated with the drawn sheet and its corresponding prescription order. The scanner 916 may scan both the top and bottom of the drawn sheet to verify that only a single sheet has been drawn. This may be compared against one or more than one previous scan, such as a scan completed while the drawn sheet was resting at the bottom of the stack of printed literature on lower shelf 708. Such a comparison may confirm that the correct sheet has been drawn, that a single sheet has been drawn, and/or that the desired number of sheets have arrived at scanner 916.

Where it is determined that there are additional sheets associated with the drawn sheet at block 1626, the control unit 316 at block 1628 determines whether all other sheets associated with the drawn sheet have been drawn from the paper collator 306. If other sheets remain in the paper collator 306, the method reverts to block 1624.

When it is determined that there are no other sheets associated with the drawn sheet at block 1626, or when it is determined that all other sheets associated with the drawn sheet have been drawn at block 1628, the method advances to block 1630. At block 1630, the scanner module 1502 may again communicate with the scanner 916 to scan each drawn sheet to confirm that such sheets are all correctly associated with the desired prescription order. If an anomaly is found at block 1630 and not all of the drawn sheets are associated with the desired prescription order, the drawn sheets are rejected at block 1632. However, where all of the drawn sheets are verified as belonging to the desired print job for a prescription order at block 1630, the method advances to block 1634.

At block 1634, the fold/unfold module 1504 of the control unit 316 determines whether the print job should be folded or remain unfolded. As discussed above, such a determination may be made based on the page count of the print job, and may have occurred earlier in the methodology. Where it is determined that the print job should remain unfolded, the print job is routed to the unfolded paper fixture stage 310 at block 1636. However, where it is determined that the print job should be folded, the print job is routed to the folded paper fixture stage 314 at step 1638. In either case, at step 1640, the robot module 1506 instructs the robot 312 to pick the print job and place it with its corresponding prescription order in the packing device 142 or the unit of use packing device 144.

Figure 17:
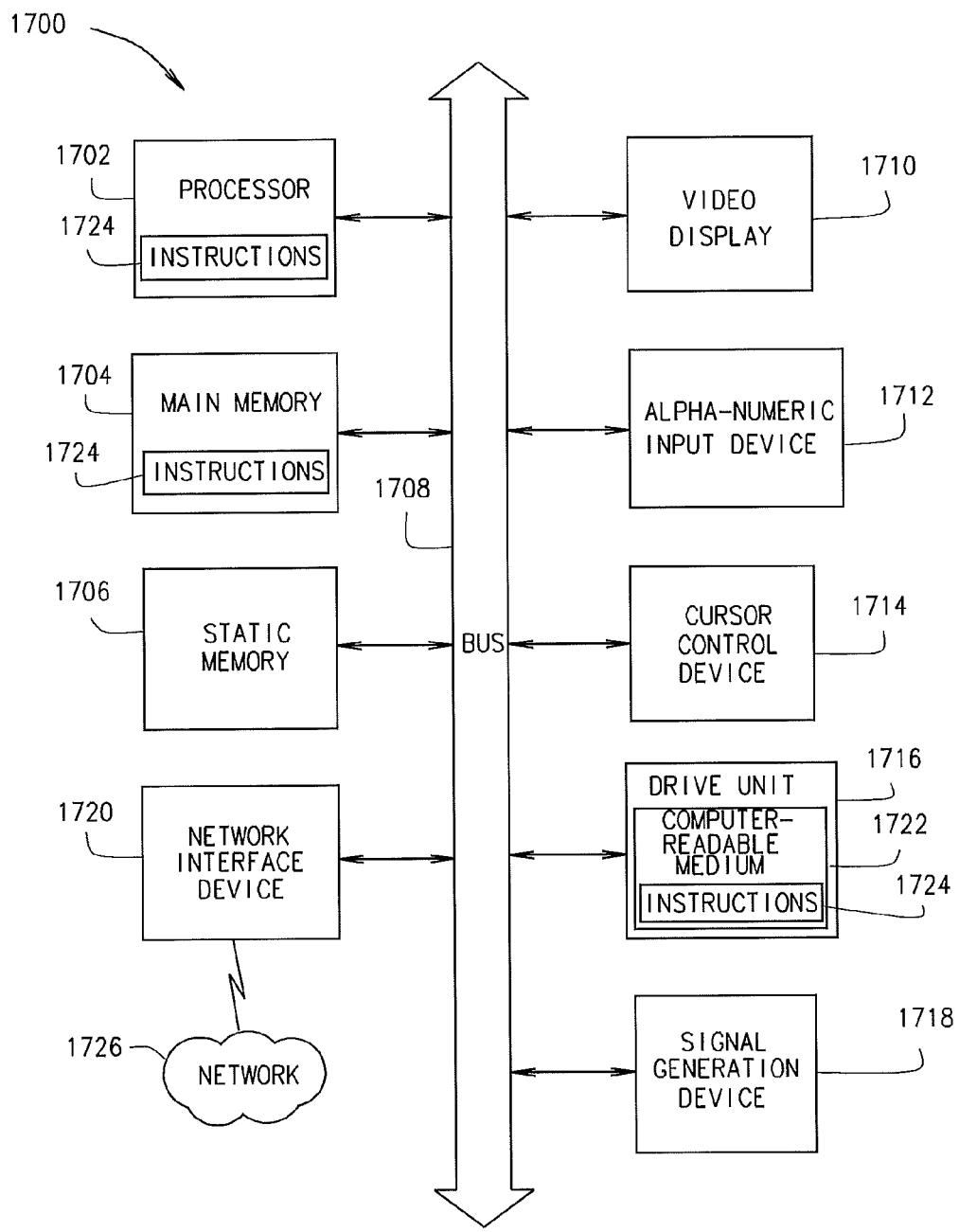
FIG. 17 is a block diagram of a machine in the example form of a computer system within which a set of instructions for causing the machine to perform any one or more of the methodologies discussed herein may be executed or stored.

FIG. 17 shows a block diagram of a machine in the example form of a computer system 1700 within which a set of instructions may be executed causing the machine to perform any one or more of the methods, processes, operations, or methodologies discussed herein. The devices 102, 106, 122-144, 300, for example, may include the functionality of the one or more computer systems 1700.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1700 includes a processor 1702 (e.g., a central processing unit (CPU) a graphics processing unit (GPU) or both), a main memory 1704 and a static memory 1706, which communicate with each other via a bus 1708. The computer system 1700 further includes a video display unit 1710 (e.g., a liquid crystal display (LCD) or a cathode ray tube (CRT)). The computer system 1700 also includes an alphanumeric input device 1712 (e.g., a keyboard), a cursor control device 1714 (e.g., a mouse), a drive unit 1716, a signal generation device 1718 (e.g., a speaker) and a network interface device 1720.

The drive unit 1716 includes a computer-readable medium 1722 on which is stored one or more sets of instructions (e.g., software 1724) embodying any one or more of the methodologies or functions described herein. The software 1724 may also reside, completely or at least partially, within the main memory 1704 and/or within the processor 1702 during execution thereof by the computer system 1700, the main memory 1704 and the processor 1702 also constituting computer-readable media.

The software 1724 may further be transmitted or received over a network 1726 via the network interface device 1720.

While the computer-readable medium 1722 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and subsystems and the like. All references to such and the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof) and instructions (e.g., software) which co-act with one another to perform operation(s) disclosed herein. In addition, any one or more of the electric devices may be configured to execute a computer-program that is embodied in a computer readable medium that is programmed to perform any number of the functions and features as disclosed. The computer readable medium may be non-transitory or in any form readable by a machine or electrical component The inventive subject matter may be represented in a variety of different embodiments of which there are many possible permutations.

The present disclosure makes reference to a robot and words of similar import. A robot can be a machine capable of carrying out a complex series of actions automatically. These complex series of actions may include picking up, orientating, positioning and/or releasing a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, e.g., a robot may move location, have an articulated arm, have grasping structures that replicate like fingers and do not damage containers, and the like.

In an example embodiment, pharmaceutical filling system includes a control device, a paper collator positioned to receive printed literature from a printer, said paper collator including at least a selectively openable upper shelf and a lower shelf, at least one of a folded paper fixture stage and an unfolded paper fixture stage, said at least one of said folded paper fixture stage and said unfolded paper fixture stage positioned to receive individual jobs of printed literature from the paper collator, a paper conveyance mechanism for mating each said individual job of printed literature with its associated fulfilled prescription order; wherein the control device is operable to determine remaining capacity of the upper shelf of the paper collator, instruct the printer to hold printing of additional print jobs, instruct an upper actuator to open the upper shelf, thereby dropping printed literature supported by the upper shelf, instruct the upper actuator to close the upper shelf, and instruct the printer to continue printing additional print jobs.

In an example embodiment, a signal from a component in a pharmacy that fulfillment of a prescription order has reached a predetermined stage is received by a control unit. A printer is instructed to print literature associated with the prescription order as a print job. The capacity status of an upper shelf of a paper collator is monitored. Upon a determination that the capacity of the upper shelf is running low, the control unit instructs the printer to hold printing on additional print jobs, instructs an upper actuator associated with the upper shelf to open the paper shelf, causes printed literature supported by the upper shelf to drop toward a lower shelf of the paper collator, instructs the upper actuator to close the upper shelf, and instructs the printer to resume printing additional print jobs.

Thus, methods and systems for a paper feed system have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A pharmaceutical filling system comprising:
   a control device;
   a paper collator positioned to receive printed literature from a printer, said paper collator including at least a selectively openable upper shelf and a lower shelf;
   at least one of a folded paper fixture stage and an unfolded paper fixture stage, said at least one of said folded paper fixture stage and said unfolded paper fixture stage positioned to receive individual jobs of printed literature from the paper collator; and
   a paper conveyance mechanism for mating each said individual job of printed literature with its associated fulfilled prescription order,
   wherein the control device is operable to determine remaining capacity of the upper shelf of the paper collator, and, when it is determined that the remaining capacity of the upper shelf of the paper collator has reached a threshold, is operable to:
      instruct the printer to hold printing of additional print jobs;
      instruct an upper actuator to open the upper shelf, thereby dropping printed literature supported by the upper shelf;
      instruct the upper actuator to close the upper shelf; and
      instruct the printer to continue printing additional print jobs.

2. The system of claim 1 wherein at least one of the folded and unfolded paper fixture stages include a comb device with spaced-apart tines to allow for faster paper settling.

3. The system of claim 1 wherein the folded paper fixture stage includes a guide with a curved end portion, and one or more fingers for pushing an individual job of printed literature through the guide and around the curved end portion;
   said folded paper fixture stage also including a piston for engaging the job of printed literature at approximately its midpoint to push the midpoint of the job of printed literature between two or more rollers; and
   wherein said rollers fold the job of printed literature about its midpoint.

4. The system of claim 1 wherein the paper conveyance mechanism for mating each said individual job of printed literature with its associated fulfilled prescription order is a robot.

5. The system of claim 1 wherein a second paper conveyance mechanism is positioned between the printer and the paper collator.

6. The system of claim 1 wherein a second paper conveyance mechanism is positioned between the paper collator and the at least one of the folded and unfolded paper fixture stages.

7. The system of claim 1 wherein the control device is in communication with a sensor to determine remaining capacity of the upper shelf of the paper collator.

8. The system of claim 1 wherein the paper collator includes a drum operable to pull a sheet of printed literature from a stack of printed literature resting on the lower shelf of the paper collator.

9. The system of claim 8 further including at least one snubber positioned on the paper collator to retain the sheets of printed literature resting on the lower shelf in place except for the bottom sheet, wherein the drum is positioned to draw the bottom sheet of printed literature from the stack of printed literature via suction.

10. The system of claim 1 further including at least one scanner in communication with the control device, said at least one scanner positioned to scan at least one sheet of printed literature to determine at least one of: the prescription order with which the sheet is associated; and the number of sheets of printed literature in the print job with which the sheet is associated.

11. The system of claim 1 wherein said control device is additionally operable to confirm that only sheets in a print job of printed literature associated with a fulfilled prescription order are mated with the associated fulfilled prescription order by communicating with said at least one scanner.

12. The system of claim 1 wherein the paper collator additionally includes a selectively openable middle shelf, and lower actuators for selectively opening the middle shelf;
wherein the control device is also operable to:
instruct the lower actuator to open the middle shelf, thereby dropping printed literature which was previously dropped by the upper shelf from the middle shelf to the lower shelf; and
instruct the lower actuator to close the middle shelf.

13. The system of claim 1, wherein the controller determines whether a print job of printed literature should be sent to the folded or unfolded paper fixture stage based on the number of pages in the print job.

14. A method comprising the steps of:
receiving, by a control unit, a signal from a component in a pharmacy that fulfillment of a prescription order has reached a predetermined stage;
instructing, by the control unit, a printer to print literature associated with the prescription order as a print job;
monitoring, by the control unit, the capacity status of an upper shelf of a paper collator;
upon determining that the capacity of the upper shelf is running low, the control unit:
instructing the printer to hold printing on additional print jobs;
instructing an upper actuator associated with the upper shelf to open the paper shelf, causing printed literature supported by the upper shelf to drop toward a lower shelf of the paper collator;
instructing the upper actuator to close the upper shelf; and
instructing the printer to resume printing additional print jobs.

15. The method of claim 14 further including the steps of:
instructing, by the control unit, the paper collator to draw a sheet of printed literature from the bottom shelf;
scanning, via a scanner, the sheet drawn from the bottom shelf to confirm that the drawn sheet is associated with the prescription order;
where there are additional sheets of printed literature in the print job associated with the drawn sheet, instructing the paper collator to draw such additional sheets from the printed literature on the bottom shelf;
scanning, via the scanner, any additionally drawn sheets to confirm that said additional drawn sheets are associated with the prescription order;
mating the confirmed print job with the fulfilled prescription order via a paper conveyance mechanism.

16. The method of claim 14, further including the steps of:
determining, by the control unit, a count of the print job associated with the prescription order;
routing the print job to either a folded paper fixture stage or an unfolded paper fixture stage from the paper collator based on the page count of the print job associated with the prescription order.

17. The method of claim 16, wherein upon routing a print job to the folded paper fixture stage, the folded paper fixture stage performs the following steps:
feeding the print job into a guide that includes a curved end portion;
pushing the print job with at least one finger through the guide and around the curved end portion;
extending a piston to engage the print job at approximately its midpoint to push the midpoint of the job of printed literature between two or more rollers;
folding the print job between the rollers about the midpoint of the print job.

18. The method of claim 14 wherein a sensor allows the control unit to monitor the capacity status of the upper shelf of the paper collator.

19. The method of claim 14 wherein the paper collator draws a sheet of printed literature from a stack of printed literature resting on the lower shelf of the paper collator via a vacuum drum, and wherein at least one snubber on the paper collator retains remaining sheets of printed literature resting on the lower shelf in place except for the bottom sheet which is drawn off by the vacuum drum.

20. The method of claim 14 further including the steps of:
after the upper shelf has opened to drop printed literature toward the lower shelf, and has been re-closed:
the control device instructing a lower actuator associated with a middle shelf to open the middle shelf, causing printed literature supported by the middle shelf to drop to the lower shelf of the paper collator;
the control device instructing the lower actuator to close the middle shelf.

* * * * *